United States Patent
Bailey et al.

(10) Patent No.: US 8,623,029 B2
(45) Date of Patent: Jan. 7, 2014

(54) COMPOSITE SKULL PINS WITH REDUCED X-RAY SIGNATURE

(75) Inventors: Eric Bailey, Hampton, NH (US); Andrew Tybinkowski, Boxford, MA (US); Matthew Dickman, Chelsea, MA (US)

(73) Assignee: NeuroLogica Corp., Danvers, MA (US)

( * ) Notice: Subject to any disclaimer, the term of this patent is extended or adjusted under 35 U.S.C. 154(b) by 898 days.

(21) Appl. No.: 12/403,247

(22) Filed: Mar. 12, 2009

(65) Prior Publication Data
US 2009/0264938 A1 Oct. 22, 2009

Related U.S. Application Data

(60) Provisional application No. 61/069,104, filed on Mar. 12, 2008.

(51) Int. Cl.
A61B 19/00 (2006.01)
A61B 17/86 (2006.01)
F16B 25/00 (2006.01)

(52) U.S. Cl.
USPC .................. 606/130; 606/329; 411/386

(58) Field of Classification Search
USPC .......... 606/130, 304, 329; 600/414, 416, 417, 600/425, 526, 429; 411/386, 493, 498
See application file for complete search history.

(56) References Cited

U.S. PATENT DOCUMENTS

| | | |
|---|---|---|
| 4,169,478 A | 10/1979 | Hickmann |
| 4,397,307 A | 8/1983 | Keller |
| 4,444,179 A | 4/1984 | Trippi |
| 4,475,550 A | 10/1984 | Bremer et al. |
| 4,539,979 A | 9/1985 | Bremer |
| 4,541,421 A | 9/1985 | Iversen et al. |
| 4,612,930 A | 9/1986 | Bremer |
| 4,838,264 A | 6/1989 | Bremer et al. |
| 5,062,415 A | 11/1991 | Weatherby et al. |
| 5,122,132 A | 6/1992 | Bremer |
| 5,156,588 A | 10/1992 | Marcune et al. |
| 5,180,361 A | 1/1993 | Moore et al. |
| 5,197,965 A | 3/1993 | Cherry et al. |
| 5,254,079 A | 10/1993 | Agbodoe et al. |
| 5,302,170 A | 4/1994 | Tweardy |
| 5,318,509 A | 6/1994 | Agbodoe |
| 5,347,894 A | 9/1994 | Fischer |
| 5,437,612 A | 8/1995 | Moore et al. |
| 5,549,620 A | 8/1996 | Bremer |
| 5,632,722 A | 5/1997 | Tweardy et al. |
| 5,961,528 A | 10/1999 | Birk et al. |
| 6,045,553 A * | 4/2000 | Iversen et al. ............. 606/304 |
| 6,379,362 B1 | 4/2002 | Birk et al. |
| 6,635,064 B2 * | 10/2003 | U et al. ...................... 606/130 |
| 8,104,477 B2 * | 1/2012 | Edlauer et al. ............. 411/498 |
| 2008/0251086 A1 | 10/2008 | Dinkler |
| 2010/0059064 A1 | 3/2010 | Schüle et al. |
| 2010/0217280 A1 | 8/2010 | Schuele et al. |

FOREIGN PATENT DOCUMENTS

EP 2014251 A1 * 1/2009

* cited by examiner

*Primary Examiner* — Julian W Woo
(74) *Attorney, Agent, or Firm* — Pandiscio & Pandiscio

(57) ABSTRACT

A composite skull pin. The composite skull pin includes a core comprising a cone terminating in a distal point, the core being formed out of a substantially radiotranslucent material; and a jacket comprising a hollow cone terminating in a sharp distal point, the hollow cone of the jacket being sized and shaped so that it overlies, and closely conforms to, the exterior of the cone of the core. The jacket is formed out of a strong, hard material, and has a sufficiently small mass such that the composite skull pin has a low X-ray signature.

9 Claims, 18 Drawing Sheets

Exploded View Of Novel Composite Skull Pin Comprising Radiotranslucent Core With Selected Titanium Jacket Stainless Steel Head Frame Stainless Steel Skull Pin With Plastic Mount X-ray Scan (no frame and no skull pins)

Radiotranslucent Head Frame With Stainless Steel Skull Pins

X-ray Scan (Radiotranslucent Head Frame With Stainless Steel Skull Pins)

X-ray Scan (Radiotranslucent Head Frame With Titanium Skull Pins)

Exploded View Of Novel Composite Skull Pin Comprising Radiotranslucent Core With Selected Titanium Jacket Radiotranslucent Core
Of The Composite
Skull Pin Enlarged View Of Titanium Jacket For The Composite Skull Pin Enlarged View Of Titanium Jacket For The Composite Skull Pin X-ray Scan (Radiotranslucent Head Frame With Titanium Jacket Skull Pins)

Alternative Construction For The Novel Skull Pin
Comprising Carbon Graphite Core With Titanium Jacket

COMPOSITE SKULL PINS WITH REDUCED X-RAY SIGNATURE

REFERENCE TO PENDING PRIOR PATENT APPLICATION

This patent application claims benefit of pending prior U.S. Provisional Patent Application Ser. No. 61/069,104, filed Mar. 12, 2008 by Eric Bailey et al. for SKULL PINS WITH REDUCED X-RAY SIGNATURE, which patent application is hereby incorporated herein by reference.

FIELD OF THE INVENTION

This invention relates to surgical procedures in general, and more particularly to intracranial surgical procedures.

BACKGROUND OF THE INVENTION

In many situations it may be necessary to perform an intracranial surgical procedure. By way of example but not limitation, a patient may have suffered a large hemorrhagic stroke and may require accumulated blood to be removed from the interior of the skull so as to relieve pressure on the brain. Or the patient may have developed a tumor which requires removal. Or the patient may have suffered a cerebral injury which requires surgical intervention.

Regardless of the patient's underlying condition and the specific surgical procedure which is to be performed, intracranial surgical procedures typically share a number of common aspects.

For one thing, due to the anatomy involved, intracranial surgical procedures generally require opening the skull at one or more locations, and then accessing specific sites within the interior of the skull in order to effect a desired surgical procedure.

Furthermore, in view of the delicate neurological tissues present in this region of the body, it is often necessary to stabilize the patient's head with some sort of external framework during the surgical procedure. This external framework generally comprises a multi-dimensional frame which is positioned alongside different surfaces of the head, and a plurality of skull pins which extend from the frame into engagement with the skull. By providing the skull pins with sharp distal tips, and by configuring the frame so that the skull pins are directed into the skull from a variety of different angles, the skull can be stabilized during the surgical procedure. See, for example, FIG. 1, which shows a head frame (formed out of stainless steel) offered by Pro Med Instruments GmbH of Freiburg, Germany under the trade name DORO™, and FIG. 2, which shows a skull pin (formed out of a stainless steel pin with a plastic mount) offered by Pro Med Instruments GmbH under the trade name DORO™.

Additionally, since direct visualization is, at best, generally quite limited within the intracranial spaces (e.g., due to the surrounding portions of the skull and, in many cases, the presence of intervening neurological tissues), it is frequently necessary (or, at the very least, highly desirable) to utilize scanners (e.g., X-ray devices, MRI machines, ultrasound imagers, etc.) before, during and after the surgical procedure. Such scanners permit visualization of internal tissue structures even where direct visualization is not possible. In this respect it should be appreciated that the use of such scanners prior to, during and immediately following the surgical procedure can be extremely important in intracranial surgery, due to the restricted fields of view, delicate neurological tissues and navigation requirements. This is particularly true during the intracranial procedure itself. In this respect it should also be appreciated that X-ray devices (e.g., CT machines, C-arm fluoroscopes, etc.) are generally the most desirable type of scanner for use during intracranial surgery, due to the high quality of their images, the ready availability of such devices within the operating suite, etc. MRI scanners are generally not preferred for intraoperative use for a variety of reasons, including the need to remove metal objects from the region of the scanner, etc.

Unfortunately, the need to use these X-ray devices during surgery complicates the design of the aforementioned head frame and skull pins. This is because forming the head frame and skull pins out of stainless steel (the traditional material of choice for operating room frames) dramatically undermines the quality of the X-ray image due to the enormous X-ray signature of stainless steel. See, for example, FIG. 3, which shows a typical X-ray image where no head frame and skull pins are present. Where the head frame and skull pins are formed out of stainless steel, large sections of the X-ray image (i.e., those sections which are aligned with the head frame and/or skull pins) are obscured and hence effectively unusable.

In view of the foregoing, attempts have been made to fabricate the head frame and skull pins out of radiotranslucent materials. Thus, and looking now at FIG. 4, there is shown another system offered by Pro Med Instruments GmbH of Freiburg, Germany under the trade name DORO™, wherein the head frame is made out of carbon graphite (a material which is substantially radiotranslucent) and only the skull pins are made out of stainless steel. As can be seen in FIG. 5, this approach significantly improves the quality of the X-ray images. However, the presence of the stainless steel skull pins in the X-ray field still creates a significant loss of image.

To this end, attempts have been made to fabricate the skull pins out of radiotranslucent materials. Unfortunately, carbon graphite (the material used to fabricate the radiotranslucent head frame) does not provide a satisfactory skull pin, since carbon graphite is too brittle to form the strong, sharp distal tips needed to penetrate into the skull. Attempts to use other radiotranslucent materials (e.g., various plastics) have also proven to be unsatisfactory. As a result, skull pins are frequently formed out of metals (e.g., titanium) which have an X-ray signature which is lower than the X-ray signature of stainless steel. While forming skull pins out of titanium generally results in X-ray images superior to the images formed when using skull pins formed out of stainless steel, there is still substantial image loss due to the X-ray signature of the titanium skull pins. See FIG. 6.

There is, therefore, a substantial need for a new approach for forming skull pins which have all of the strength and integrity needed to effectively penetrate and grip the skull, yet which have a sufficiently small X-ray signature so as to permit the creation of X-ray images of high quality.

SUMMARY OF THE INVENTION

The present invention provides a novel composite skull pin having all of the strength and structural integrity needed to effectively penetrate and grip the skull, yet which also provides a reduced X-ray signature so as to permit the creation of X-ray images of superior quality.

In one form of the invention, there is provided a composite skull pin comprising:

a core comprising a cone terminating in a distal point, the core being formed out of a substantially radiotranslucent material; and a jacket comprising a hollow cone terminating in a sharp distal point, the hollow cone of the jacket being sized and shaped so that it overlies, and closely conforms to, the exterior of the cone of the core, the jacket being formed out of a strong, hard material, and further wherein the jacket has a sufficiently small mass such that the composite skull pin has a low X-ray signature.

In another form of the invention, there is provided a method for scanning the head of a patient, comprising:

providing a head frame which is at least partially radiotranslucent, and providing a composite skull pin, where the composite skull pin comprises:

a core comprising a cone terminating in a distal point, the core being formed out of a substantially radiotranslucent material; and a jacket comprising a hollow cone terminating in a sharp distal point, the hollow cone of the jacket being sized and shaped so that it overlies, and closely conforms to, the exterior of the cone of the core, the jacket being formed out of a strong, hard material, and further wherein the jacket has a sufficiently small mass such that the composite skull pin has a low X-ray signature; and securing the head of a patient to the head frame using the composite skull pin.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
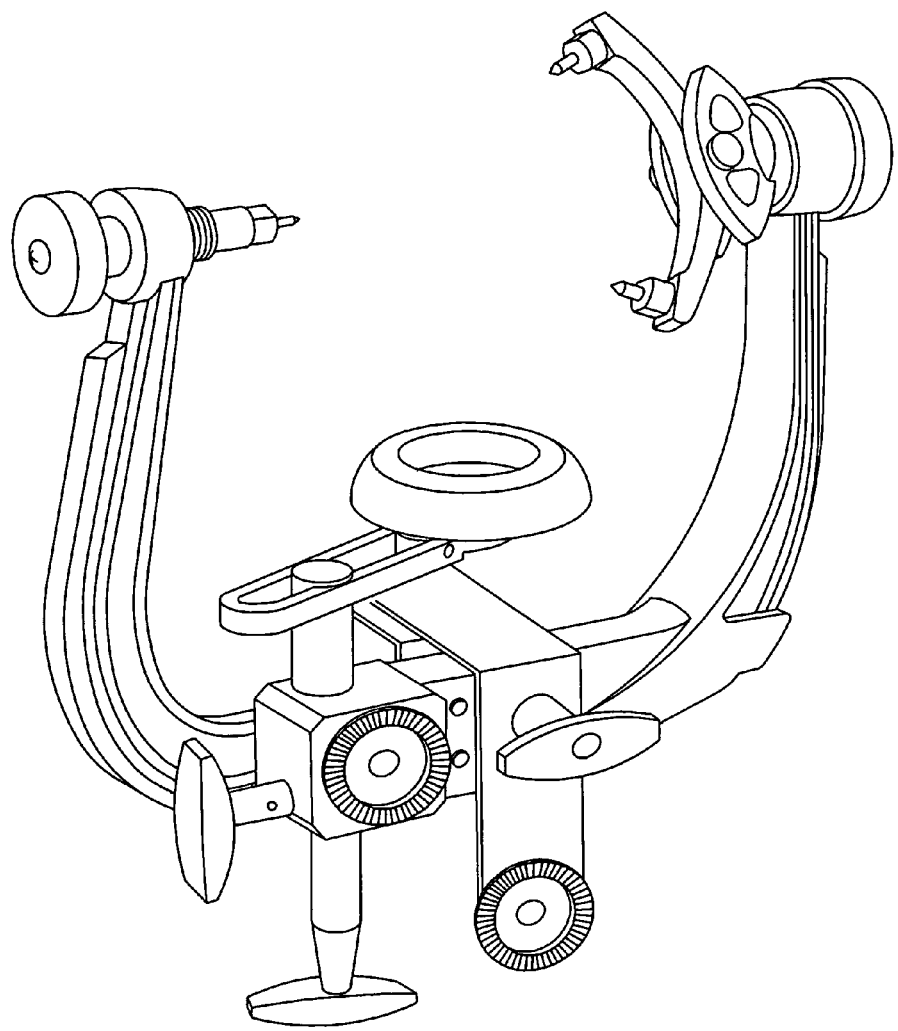
FIG. 1 is a schematic view showing a prior art stainless steel head frame.
Figure 2:
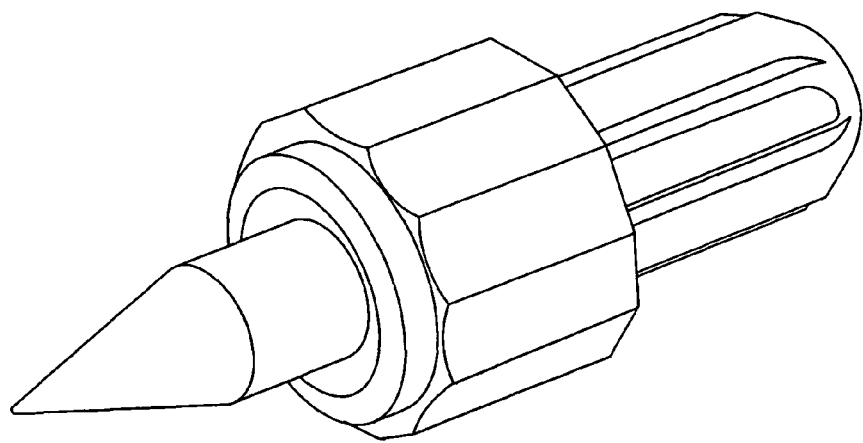
FIG. 2 is a schematic view showing a prior art skull pin comprising a stainless steel pin with a plastic mount.
Figure 3:
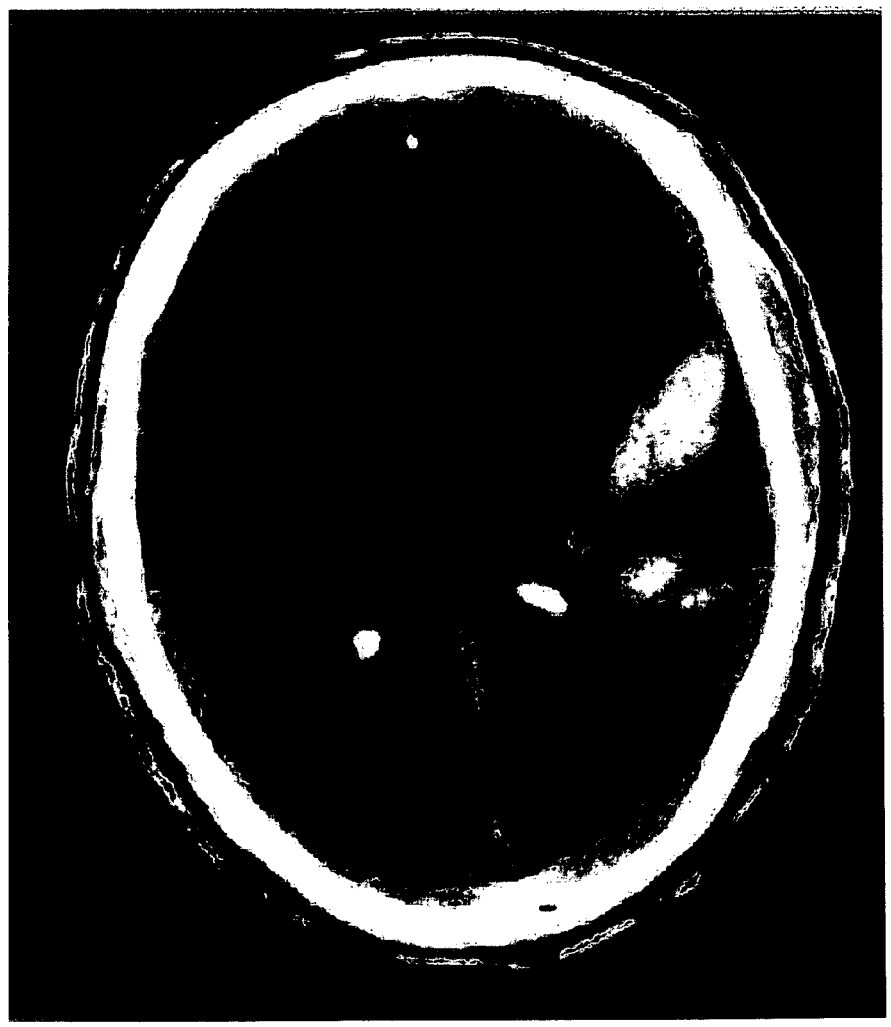
FIG. 3 is a schematic view showing a typical X-ray image where no head frame and skull pins are present.
Figure 4:
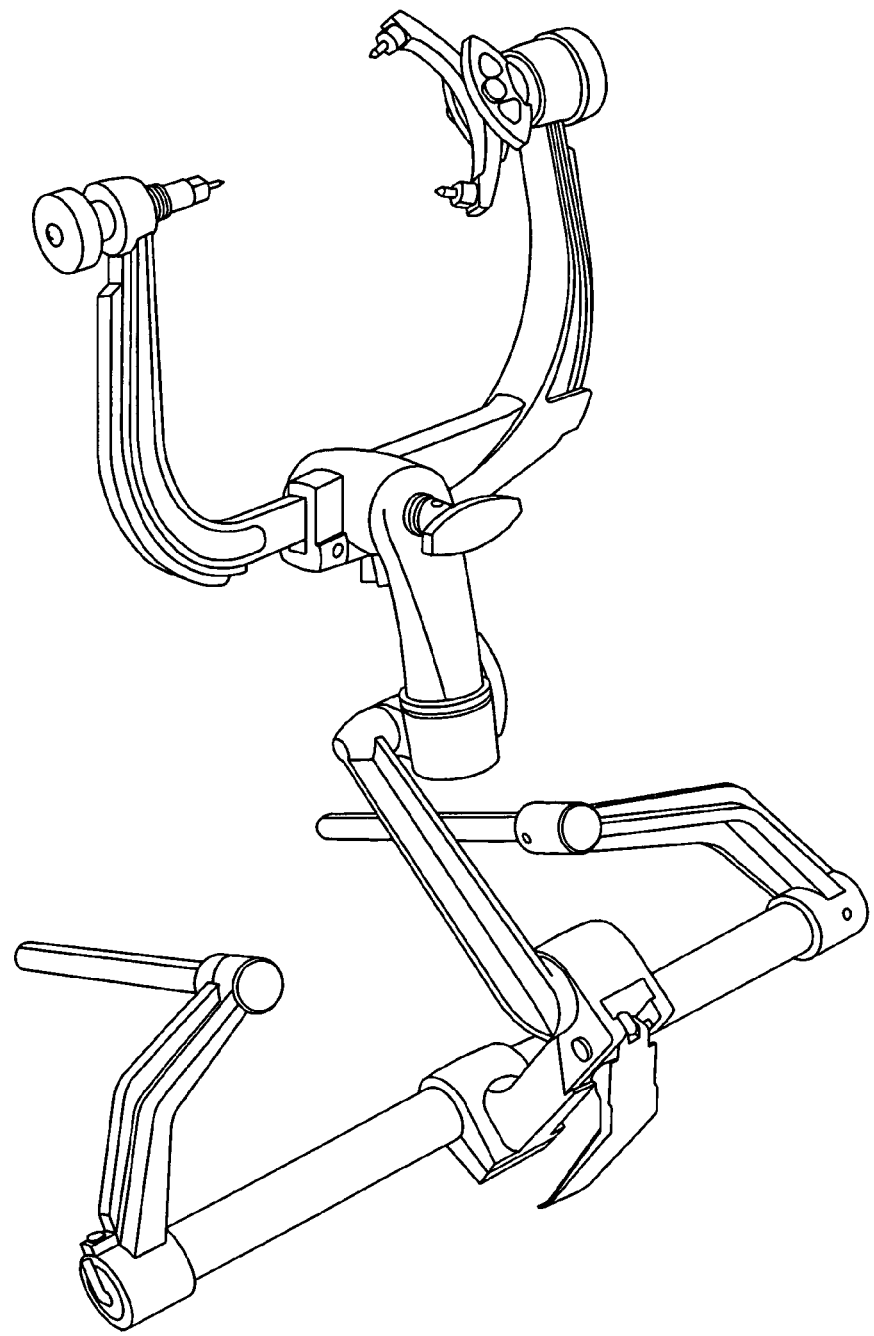
FIG. 4 is a schematic view showing a prior art system comprising a radiotranslucent head frame and stainless steel skull pins.
Figure 5:
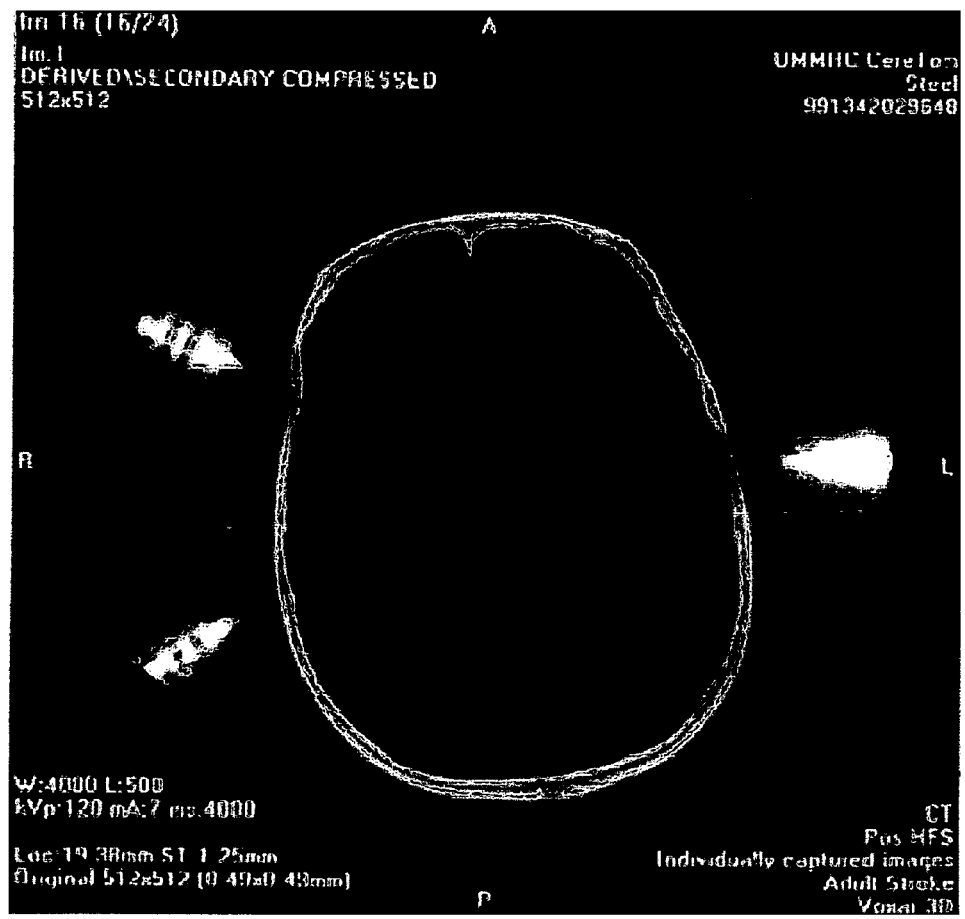
FIG. 5 is a schematic view showing a typical X-ray image where the head frame is formed out of a radiotranslucent material and the skull pins are formed out of stainless steel.
Figure 6:
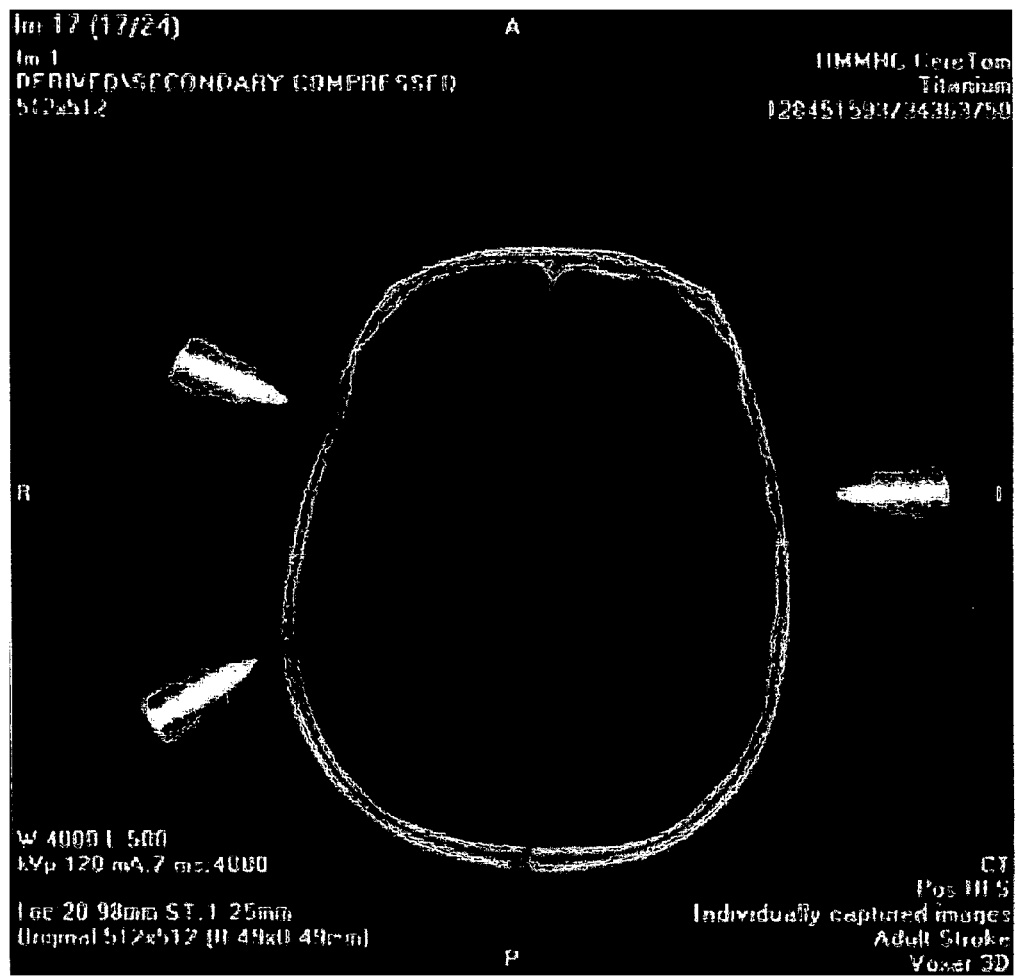
FIG. 6 is a schematic view showing a typical X-ray image where the head frame is formed out of a radiotranslucent material and the skull pins are formed out of titanium.
Figure 7:
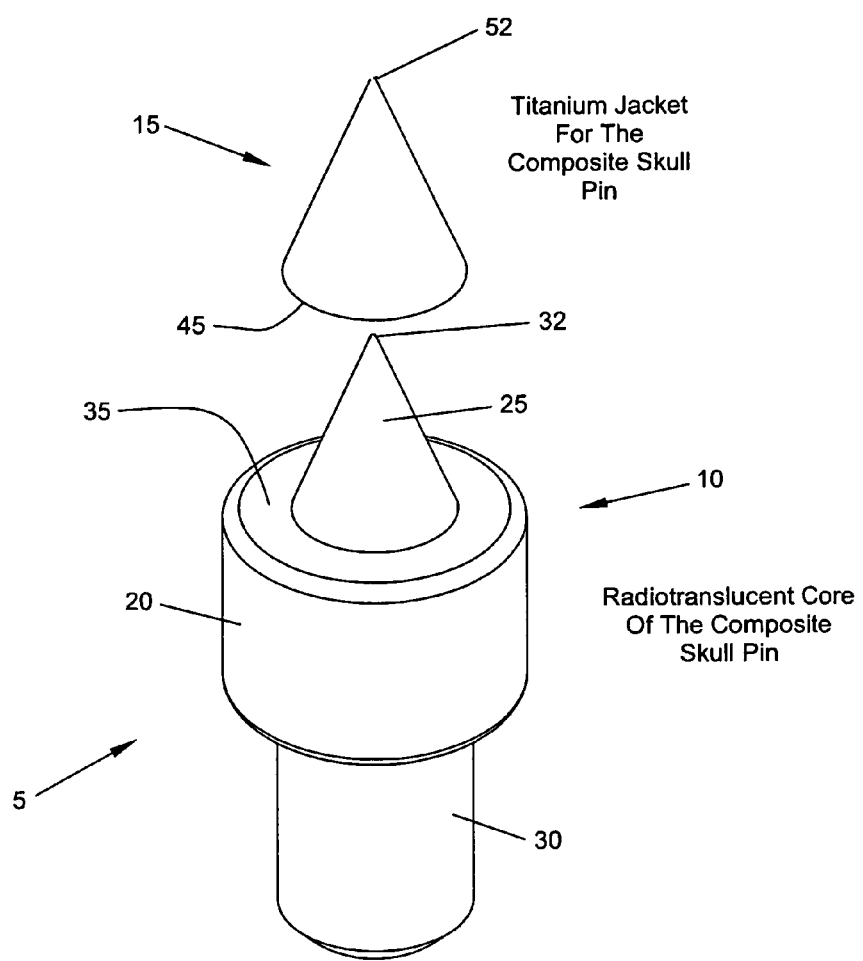
FIG. 7 is an exploded schematic view showing a novel composite skull pin formed in accordance with the present invention.
Figure 8:
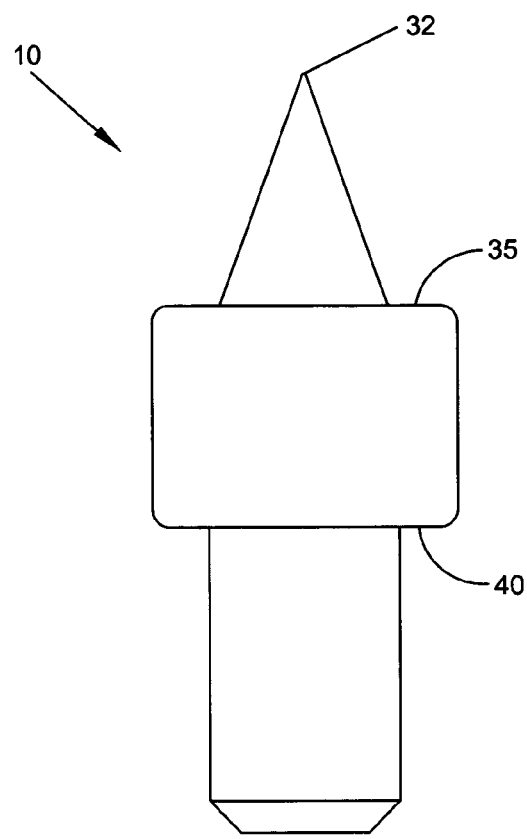
FIG. 8 is a schematic side view showing the radiotranslucent carbon graphite core of the composite skull pin shown in FIG. 7.
Figure 9:
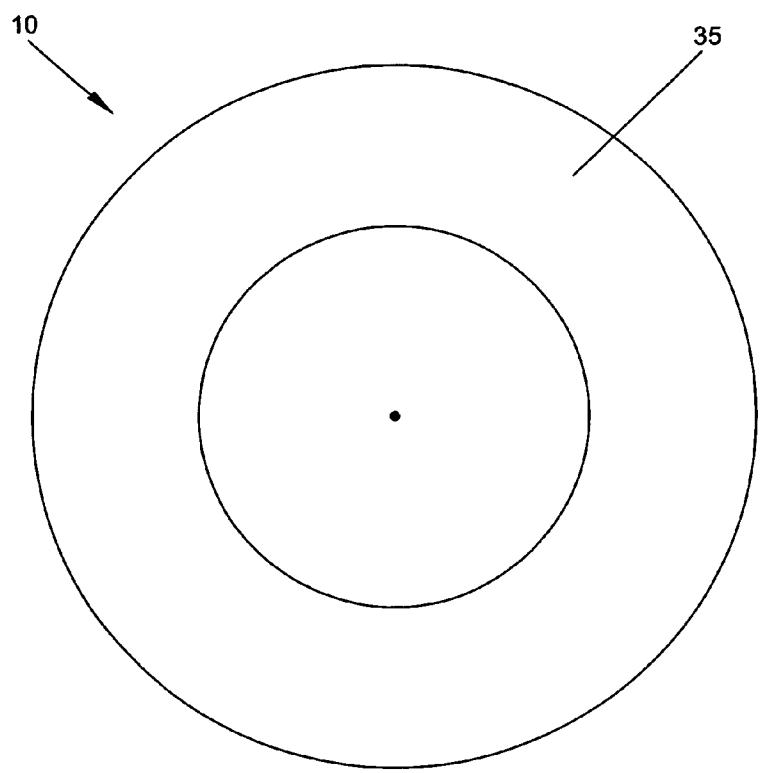
FIG. 9 is a schematic distal end view of the radiotranslucent carbon graphite core shown in FIG. 8.
Figure 10:
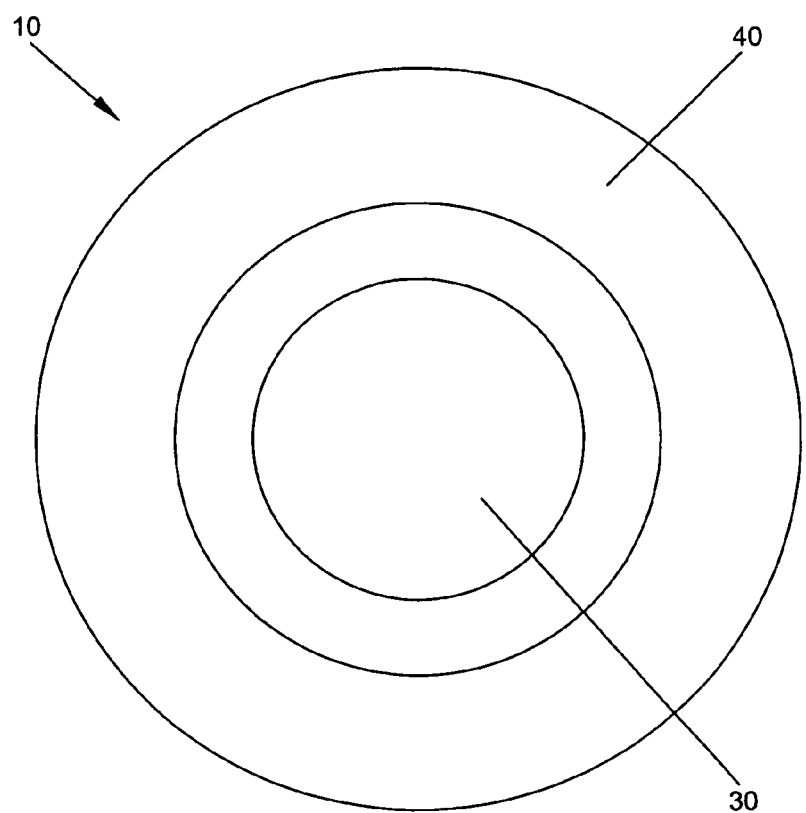
FIG. 10 is a schematic proximal end view of the radiotranslucent carbon graphite core shown in FIG. 8.
Figure 11:
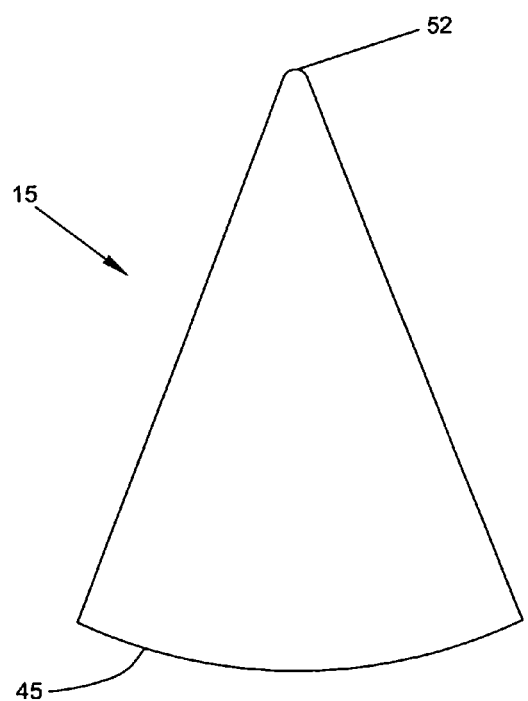
FIG. 11 is a schematic view showing the titanium jacket of the composite skull pin shown in FIG. 7.
Figure 12:
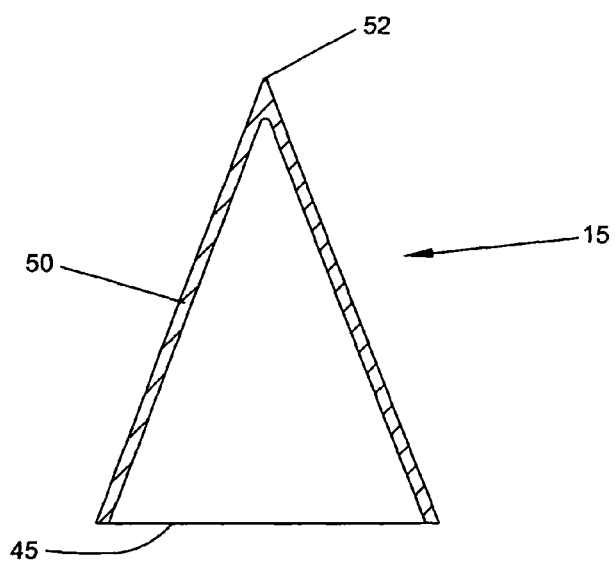
FIG. 12 is a schematic sectional view of the titanium jacket shown in FIG. 11.

Looking now at FIGS. 7-12, there is shown a novel composite skull pin 5 formed in accordance with the present invention. Composite skull pin 5 generally comprises a carbon graphite core 10 carrying, over a selected portion of its exterior, a titanium jacket 15.

Carbon graphite core 10 makes up the primary mass of composite skull pin 5 and is effectively radiotranslucent. In one preferred form of the invention, carbon graphite core 10 comprises a cylindrical body 20 having a cone 25 on its distal end and a cylinder 30 on its proximal end. Cone 25 terminates in a sharp tip 32 on its distal end. An annular shoulder 35 is formed at the intersection of cylindrical body 20 and cone 25, and an annular shoulder 40 is formed at the intersection of cylindrical body 20 and cylinder 30. Annular shoulder 35 preferably provides a stop or support for the base 45 of titanium jacket 15, and annular shoulder 40 preferably provides a stop or support for mounting composite skull pin 5 in a head frame, as will be apparent to those skilled in the art in view of the present disclosure.

Titanium jacket 15 preferably covers only the distal tip of carbon graphite core 10. In one preferred form of the invention, titanium jacket 15 comprises a hollow cone 50 for covering cone 25 of carbon graphite core 10. Hollow cone 50 terminates in a sharp tip 52 on its distal end. Hollow cone 50 is sized and shaped so that it can overlie, and closely conform to, the exterior of cone 25. Preferably, base 45 of titanium jacket 15 engages annular shoulder 35 of carbon composite core 10 when titanium jacket 15 is mounted on cone 25 of carbon graphite core 10, so that the primary load of engaging the skull of the patient is born by annular shoulder 35. Alternatively, hollow core 50 of titanium jacket 15 and core 20 of carbon graphite core 10 may be formed so that the primary load of engaging the skull of the patient is distributed across substantially the entire surface area of cone 20 of carbon graphite core 10.

Figure 13:
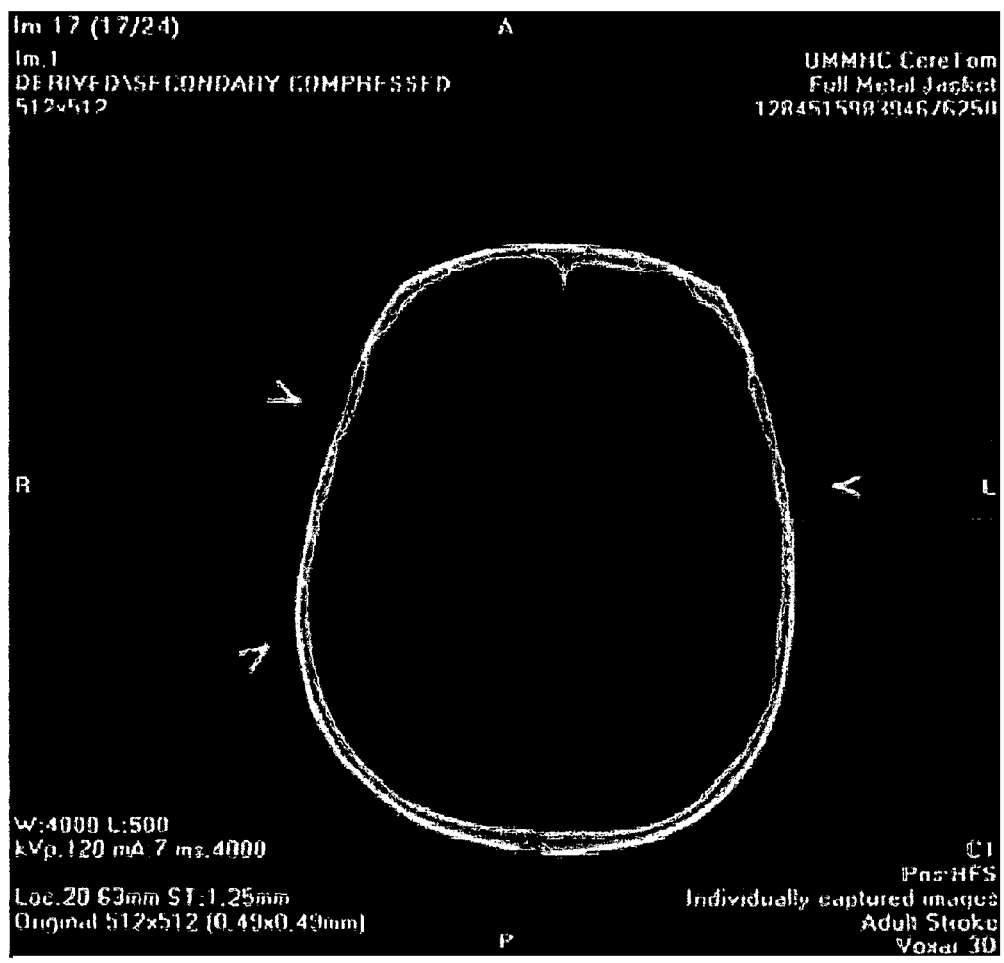
FIG. 13 is a schematic view showing a typical X-ray image where the head frame is formed out of a radiotranslucent material and the skull pins are formed with the composite construction shown in FIG. 7.
Figure 14:
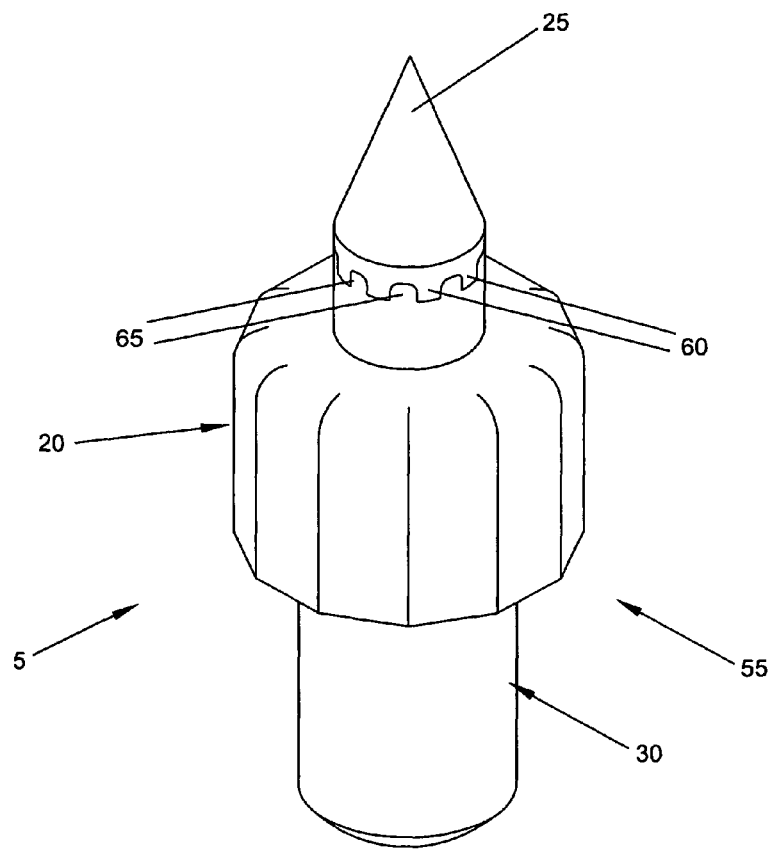
FIG. 14 is an exploded schematic view showing an alternative form of composite skull pin formed in accordance with the present invention.
Figure 15:
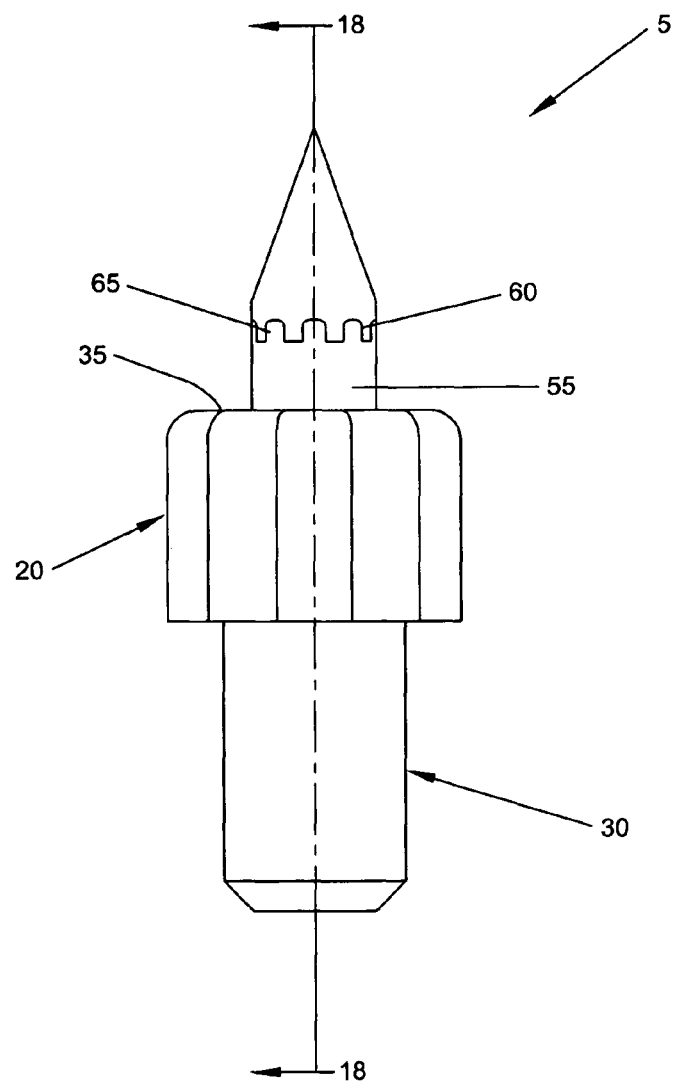
FIG. 15 is a schematic side view showing the composite skull pin shown in FIG. 14.
Figure 16:
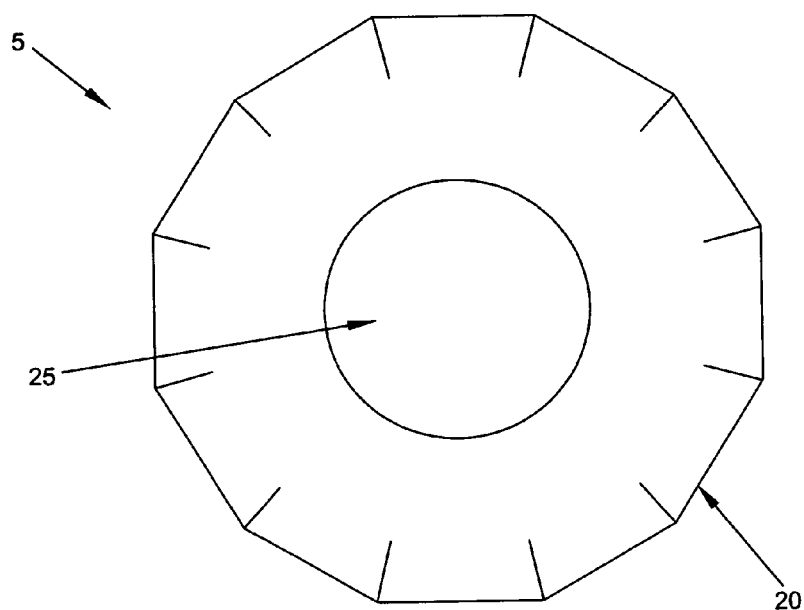
FIG. 16 is a schematic distal end view of the composite skull pin shown in FIG. 14.
Figure 17:
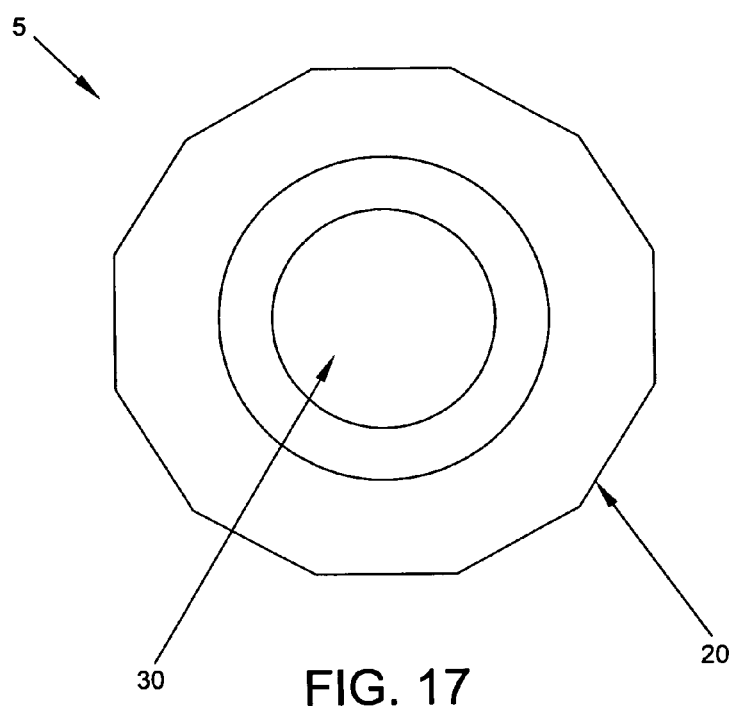
FIG. 17 is a schematic proximal end view of the composite skull pin shown in FIG. 14.
Figure 18:
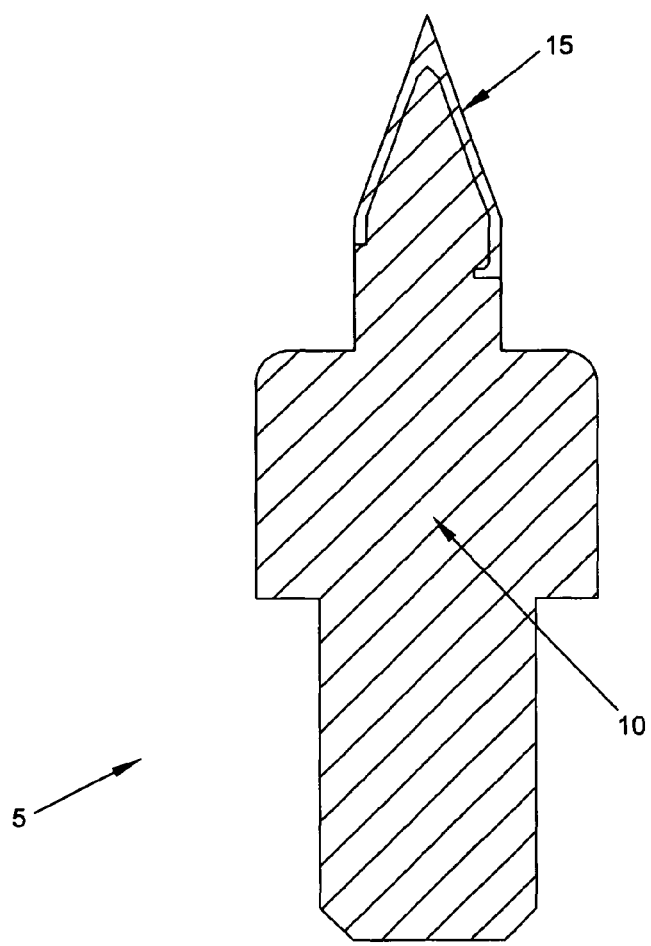
FIG. 18 is a schematic sectional view, taken along line 18-18 of FIG. 17, showing the composite skull pin shown in FIG. 14.

Titanium jacket 15 provides the sharp distal tip of composite skull pin 5 with the strength and integrity needed to penetrate the scalp and grip the skull of a patient. However, titanium jacket 15 is preferably very thin, e.g., only about 0.010 inches thick or less, or some other minimal thickness, so that the titanium jacket constitutes very little mass and hence presents a minimal X-ray signature. See, for example, FIG. 13, which shows the X-ray image made using a composite skull pin formed in accordance with the present invention, wherein the core of the composite skull pin comprises carbon graphite and the distal tip jacket comprises titanium. Note how the X-ray image of FIG. 13 is essentially devoid of skull pin artifacts, due to the use of the composite skull pins of the present invention.

Titanium jacket 15 may be secured to carbon graphite core 10 using glue or epoxy, or the various parts may be machined or otherwise fabricated so that no glue or epoxy is needed.

Thus, the novel skull pin of the present invention effectively comprises a composite structure, utilizing two different components, formed out of two different materials, so as to provide a superior skull pin. More particularly, the present invention provides a novel skull pin comprising (i) a core formed out of radiotranslucent carbon graphite, and (ii) a thin distal jacket formed out of strong, hard titanium. This permits the skull pin to have a low X-ray signature, since the major portion of the skull pin (i.e., the core) is formed out of radiotranslucent carbon graphite. At the same time, this construction permits the skull pin to have the strong, hard point needed to penetrate the scalp and grip the skull, since the distal tip of the core is covered by a thin jacket of titanium. The titanium jacket is deliberately made very thin (e.g., about 0.010 inches thick or some other minimal thickness) in order to constitute very little mass and hence present only a minimal X-ray signature.

See also FIGS. 14-18, which shows an alternative skull pin 5 also utilizing the novel composite construction of the present invention. In the composite skull pin 5 shown in FIGS. 14-18, cone 25 of carbon graphite core 10 is not mounted directly on cylindrical body 20 of carbon graphite core 10; rather, it is mounted to the distal end of a cylinder 55 which is itself mounted to cylindrical body 20. Furthermore, titanium jacket 15 is not does not engage annular shoulder 35 of carbon graphite core 10; rather, the proximal end of titanium jacket 15 comprises a plurality of fingers 60 which interlock with a plurality of counterpart fingers 65 formed on cylinder 55 so as to support titanium jacket 15 about cone 25. As a result of this construction, the primary load of engaging the skull of the patient is born by the interface of fingers 60, 65, i.e. it is not born by the distal tip of carbon graphite core 10.

If desired, the radiotranslucent core of the present invention can be fabricated out of a suitable radiotranslucent material other than carbon graphite, and/or the strong, hard distal tip jacket of the present invention can be fabricated out of a material other than titanium, e.g., a synthetic plastic material marketed by Integra LifeSciences Corporation of Plainsboro, N.J. under the trade name Sapphire™.

Modifications of the Preferred Embodiments

It should be understood that many additional changes in the details, operation, steps and arrangements of elements, which have been herein described and illustrated in order to explain the nature of the present invention, may be made by those skilled in the art while still remaining within the principles and scope of the invention.

What is claimed is:

1. A method for scanning the head of a patient, comprising: providing a head frame which is at least partially radiotranslucent, and providing a composite skull pin, wherein the composite skull pin comprises:
   a core comprising a cylindrical body having a cone on its distal end, wherein the cone terminates in a distal point, and further wherein the core is formed out of a substantially radiotranslucent material; and
   a hollow conical jacket terminating in a sharp distal point, the hollow conical jacket being sized, shaped and positioned so that it overlies, and closely conforms to, the exterior of the cone of the core, the hollow conical jacket being formed out of a strong, hard material, and further wherein the hollow conical jacket has a sufficiently small mass such that the composite skull pin has a low X-ray signature; and
   securing the head of a patient to the head frame using the composite skull pin.

2. A method according to claim 1 wherein the core is formed out of carbon graphite.

3. A method according to claim 1 wherein the hollow conical jacket is formed out of a non-radiotranslucent material.

4. A method according to claim 1 wherein the hollow conical jacket is formed out of titanium.

5. A method according to claim 1 wherein the hollow conical jacket is formed out of a synthetic plastic material.

6. A method according to claim 1 wherein the hollow conical jacket has a thickness of about 0.010 inches or less.

7. A method according to claim 1 wherein the cylindrical body of the core has a cylinder extending proximally from the cylindrical body, with a first annular shoulder being formed at the intersection of the cylindrical body and the cone, and a second annular shoulder being formed at the intersection of the cylindrical body and the cylinder.

8. A method according to claim 7 wherein the base of the hollow conical jacket engages the first annular shoulder of the core.

9. A method according to claim 1 wherein the cylindrical body of the core has a cylinder at its distal end, wherein the cone is mounted to the cylinder, and further wherein the base of the hollow conical jacket engages portions of the cylinder.

* * * * *